United States Patent [19]
Dolisi

[11] Patent Number: 5,986,162
[45] Date of Patent: Nov. 16, 1999

[54] BARRIER PROTECTOR FOR PROTECTING A SURGICAL PATIENT FROM CHEMICAL BURNS CAUSED BY TOPICAL APPLICATION OF ANTISEPTICS

[76] Inventor: Frank Dolisi, 21 Woodland Rd., Old Brookville, N.Y. 11545

[21] Appl. No.: 09/045,180
[22] Filed: Mar. 20, 1998
[51] Int. Cl.[6] .................................................... A61F 13/00
[52] U.S. Cl. .............................................. 602/41; 602/48
[58] Field of Search ..................... 602/41, 48; 604/890.1

[56] References Cited

U.S. PATENT DOCUMENTS

| 3,658,065 | 4/1972 | HInsch | ..................................... 128/296 |
| 4,641,643 | 2/1987 | Green | ..................................... 128/156 |

Primary Examiner—Richard J. Apley
Assistant Examiner—Kelvin Hart
Attorney, Agent, or Firm—Alfred M. Walker

[57] ABSTRACT

A surgical preparation protective barrier device includes a hollow flexible barrier pouch for preventing the spread of a caustic pre-surgical preparatory topical substances, such as for example BETADINE®. The barrier device is indented with a centrally located hole which extends through the barrier device from top to bottom to permit application of a topical antiseptic substance therethrough for topical application to a designated portion of skin defined by a hole in the pouch at a surgical site of a human or veterinary patient. The flexible barrier pouch further includes an inner compartment extending between peripherally extending walls and the centrally lowered hole. Fluid absorbent members are provided with the hollow compartment to collect and prevent the spread of the topical antiseptic beyond the boundaries of the predetermined surgical site. In use, the hollow pouch is applied to the skin by an adhesive which is placed on the skin surrounding the predetermined surgical site. The topical antiseptic is then applied in a standard fashion to the skin, wherein excess topical antiseptic collects and is absorbed by the spongy material placed within the hollow compartment of each pouch.

32 Claims, 5 Drawing Sheets

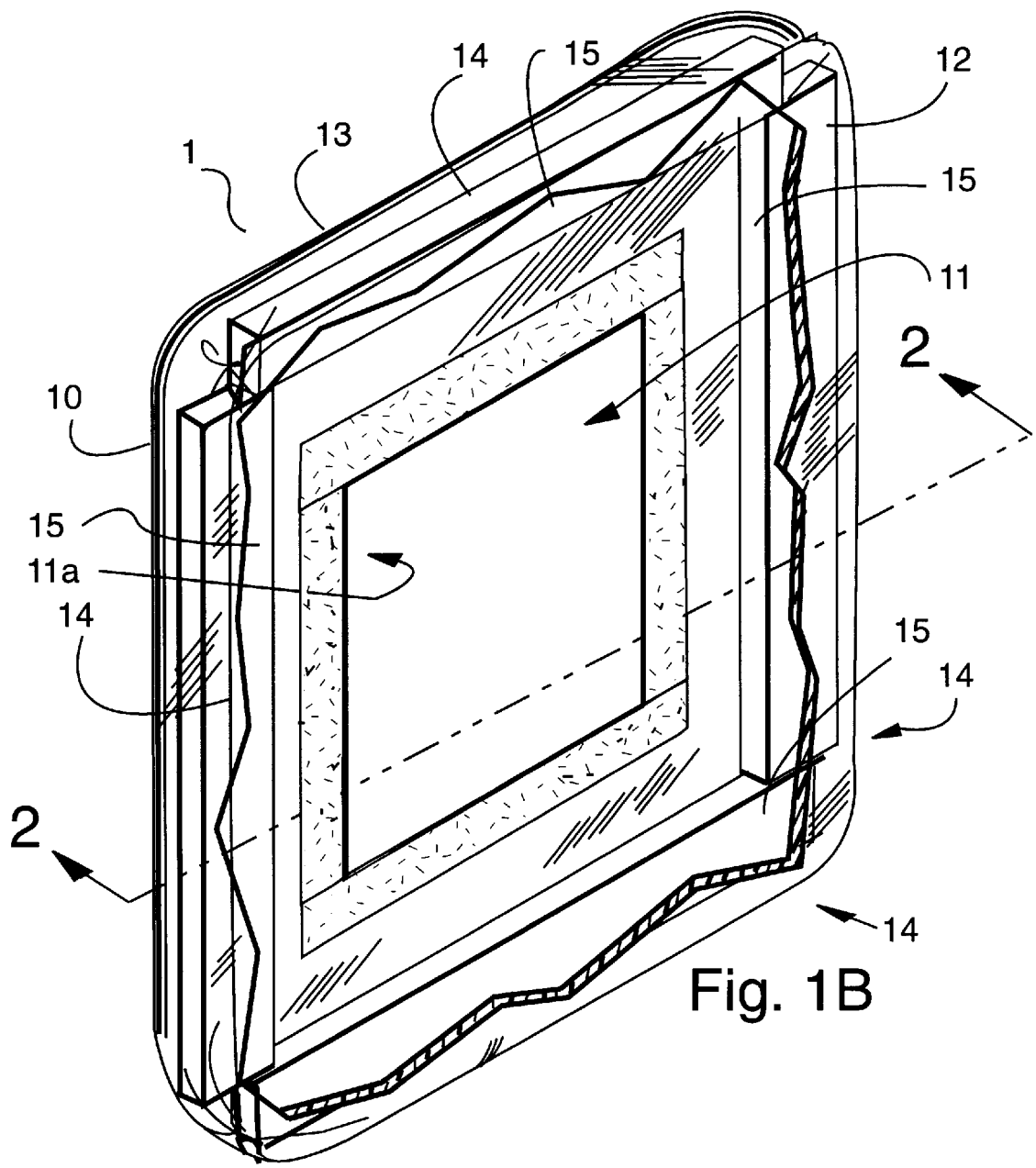
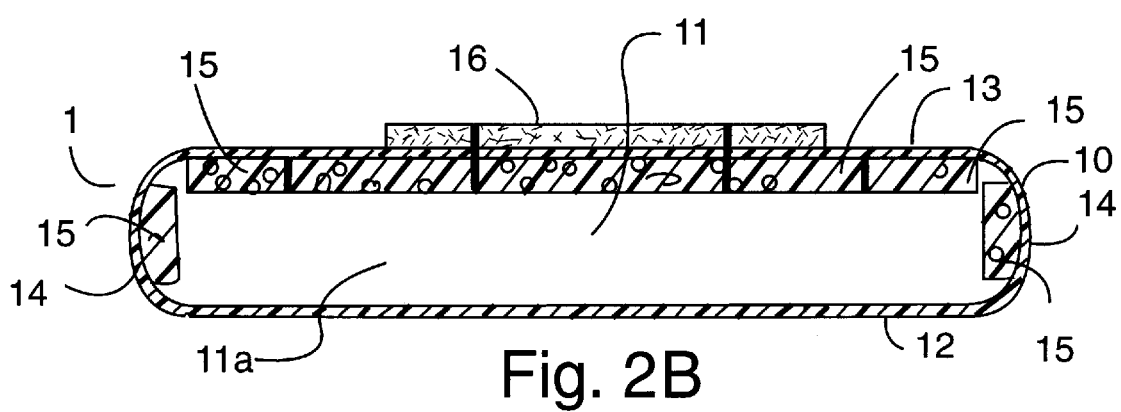
Fig. 1B
Fig. 2B

BARRIER PROTECTOR FOR PROTECTING A SURGICAL PATIENT FROM CHEMICAL BURNS CAUSED BY TOPICAL APPLICATION OF ANTISEPTICS

FIELD OF THE INVENTION

The present invention relates to surgical preparation protective devices. More particularly, the present invention relates to a template accessory barrier device for isolating a surgical patient from chemical burns caused by accumulation of caustic topically applied antiseptic solutions.

BACKGROUND OF THE INVENTION

BETADINE® is a topical antiseptic solution which is very commonly used in both the operating room and office for skin preparation prior to a surgical procedure. Skin preparation is performed in order to try and prevent post surgical infection. Two common problems encountered by the health care provider performing the preparation of the surgical site are (1) applying the BETADINE® solution to a field that is either too small or too large for the procedure and (2) allowing excess BETADINE® solution to "pool" around the dependent areas of the patient. These problems can cause a higher infection rate post operatively if the surgical field is not adequately covered. If too much BETADINE® solution is applied and the patient is "sensitive" to this chemical then a larger adverse reaction can occur. Most importantly, if excess BETADINE® solution pools in dependent areas, a severe skin reaction can occur commonly called "BETADINE burns". These chemical "burns" can cause significant morbidity to the skin and tissues of the patient.

While the present invention relates to a generally non-sterile preparation barrier device which isolates a surgical patient from chemical bums caused by exposure to topical antiseptics, sterile surgical drapes including fenestration holes placed at a surgery site have been known. Among patents for surgical drapes include U.S. Pat. No. 3,625,205 of Madden, U.S. Pat. No. 3,741,206 of Binard, U.S. Pat. No. 4,089,331 of Hartigan, U.S. Pat. No. 4,275,720 of Wichmangue, U.S. Pat. No. 5,209,243 of Glassman, as well as U.S. Pat. Nos. 5,394,891, 5,398,700 and 5,464,024 all three of Mills.

However, the surgical drapes of these patents are used as draping at a surgical field or as a device to collect gushing bodily fluids.

However, these surgical drapes are not used as a template accessory in preparing a surgical field and to prevent the harsh effects of chemical preparation of the skin of a patient with topical antiseptic.

OBJECTS OF THE INVENTION

It is therefore, an object of the present invention to provide a non-sterile accessory template for preventing topical antiseptics applied at a surgical site from spreading to non-surgical areas and accumulating for excessive periods of time.

It is also an object of the present invention to provide a barrier to the spread of caustic topical antiseptics away from a surgical site. It is yet another object of the present invention to prevent chemical bums to a surgical patient.

SUMMARY OF THE INVENTION

In keeping with those objects and others which may become apparent, the barrier protector of the present invention is designed to minimize the above problems with skin preparation. The present invention is a protective barrier device to prevent the spread of the surface flow of a topical antiseptic from beyond a predetermined surgical site. It includes a hollow pouch having an opening extending therethrough. The opening defines the boundaries of the predetermined surgical site. The hollow pouch further has an upper surface separated from a lower surface by peripherally extended wall, so that the opening extends between the upper surface and the lower surface of the hollow pouch.

The hollow pouch also has a hollow compartment between its upper surface and its lower surface. Furthermore, the hollow pouch has a structural housing which are is C-shaped in cross section but circular, rectangular, square or otherwise geometrically shaped in exterior shape.

With respect to the circular version, the three dimensional shape may be described as a hollow toroid (donut shaped) having a larger outer diameter surface and a smaller inner diameter surface, such as for example, like an uninflated automobile tire. In the case of the square or rectangular shape, the hollow pouch includes a plurality of joined longitudinally extending C-shaped members, wherein each open portion of each C-shaped member faces inward toward the opening of the hollow pouch.

The hollow compartment has at least one fluid absorbent member therein for absorbing the flowing topical antiseptic therein. Moreover, the hollow pouch has a skin adhering adhesive on its lower, body facing surface, to prevent the flow of antiseptic beyond the opening, and a removable cap layer covering the opening prior to use.

The above noted upper surface extends in a cantilevered manner away from the peripherally extending walls toward the opening. In case of a circular pouch, however, there is only one outer wall, which is a circumferentially extending wall.

In other embodiments, there are a plurality of walls defining a geometric shaped member, such as a square, or rectangular shape. In addition, the fluid absorbent member can be an absorbent fabric or a sponge.

This barrier device is intended to be applied to many surgical fields for all general and sub specialty surgical procedures utilizing topical antiseptic solutions, such as BETADINE® to prepare the surgical site. The device is applied as follows:

First, an adhesive edge extending along an annular patient-facing frame plastic pouch is placed on the skin surrounding the surgical site. Normally, the adhesive and plastic pouch is not sterile. The surgical site is then checked to assure there are no openings in the adhesive edge leading to the skin below. The recommended area to prepare the skin for surgery is thus exposed.

Thereafter, a topical antiseptic such as BETADINE®, is then applied in a standard fashion to the skin. Any excess topical antiseptic solution is then collected in the dependent collecting areas of the plastic pouch and is then absorbed by spongy material placed at the base of each pouch. Then the pouch is either removed or not removed from the surgical site.

Finally, the surgeon then applies a conventional sterile drape with its existing fenestrations and devices to collect body fluid/blood during the surgical procedure.

The barrier protector is constructed to be appropriate for all types of surgical procedures and therefore, by definition, is of various shapes and sizes. This plurality of structional configurations allows application to the head and neck, back and thorax, abdomen and pelvis, and upper and lower extremities. The simple structional configuration and non sterile nature of the barrier protector allows for it to be very cost effective. The barrier protector has the potential to decrease patient infectious and irritant morbidity. The latter also proves to be cost effective for the hospital that is self insured in regard to potential malpractice claims due to what is known commonly as "BETADINE burns" that invariably and inadvertently occur each year in many operating rooms.

BRIEF DESCRIPTION OF THE DRAWINGS

The present invention can best be understood in connection with the accompanying drawings, in which:

FIG. 1B is an isometric view of the surgical preparation protective barrier device of the present invention, shown in cutaway;

FIG. 2B of the surgical protective barrier devise as shown in FIG. 1B, is a cross sectional view taken at line "2—2" therein, with the adhesive layer on top thereof;

DETAILED DESCRIPTION OF THE PREFERRED EMBODIMENTS

Figure 1A:
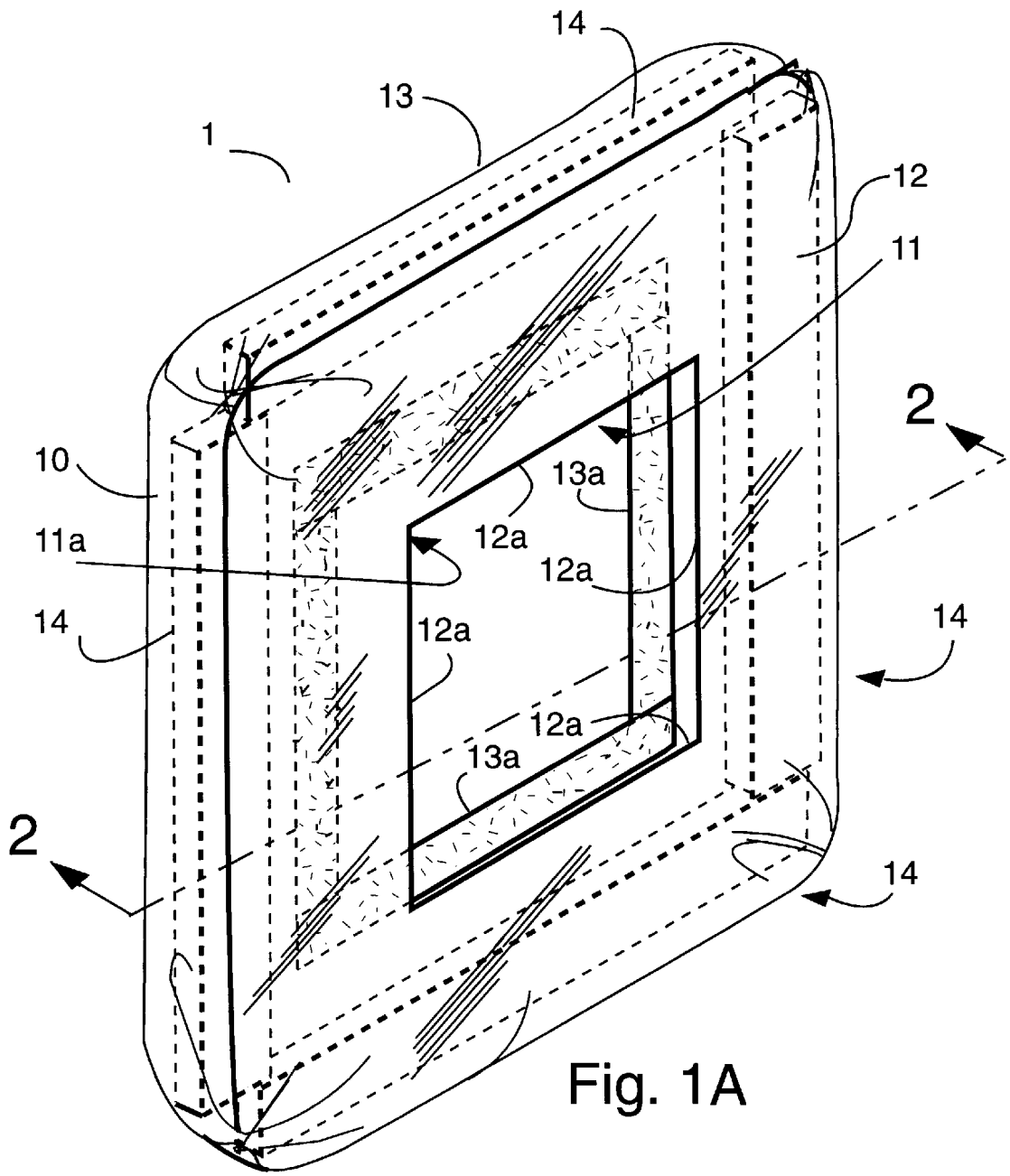
FIG. 1A is an isometric view of the surgical preparation protective barrier device of the present invention.
Figure 2A:
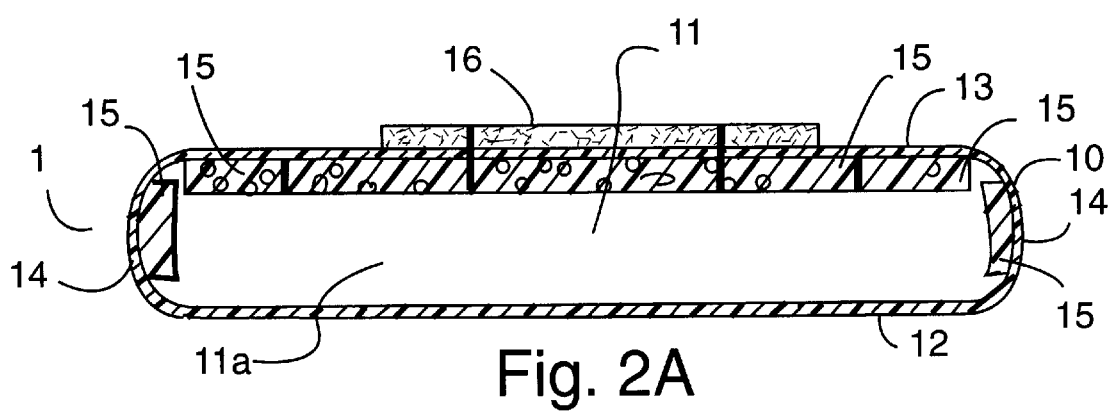
FIG. 2A is a cross sectional view of the surgical protective barrier device, as shown in FIG. 1A, taken at line "2—2" therein; with the adhesive layer on top thereof.

Surgical preparation protective barrier device 1 is a hollow pouch having a flexible barrier housing 10 for preventing the spread of caustic pre-surgical preparatory topical substances, such as for example, BETADINE.®

Barrier housing 10 is preferably made of a flexible fluid in permeable plastic, such as a vinyl or polypropylene. Barrier housing 10 is indented with a centrally located hole 11, which extends through barrier housing 10 from top upward surface 12 to bottom patient facing surface 13 to permit application of the topical substance therethrough for topical application to a designated portion of skin at a surgical site of a human or veterinary patient.

Opening 11 may be temporarily covered by a removable cap layer (not shown).

Barrier housing 10 includes at least one outer wall 14 extending along its entire exterior peripheral edge. In the case of a geometric shape, such as square-shaped housing 10 shown in FIGS. 1A, 1B or 3, or a rectangular shaped barrier housing 210 shown in FIGS. 5 and 6, the at least one outer wall 14 includes a plurality of walls 14 or 214. In case of a circular-shaped housing 110 as shown in FIG. 8, only one circumferentally extending well 114 is provided.

Walls 14 separate upper surface 12 from lower body facing surface 13, wherein upper surface 12 extends in a cantilevered fashion inward away from walls 14 to respective inner peripheral edges 12a. Likewise lower surface 13 extends inward away from walls 14 to respective inner peripheral edges 13a, wherein a hollow compartment 11a having a sideways "C-shaped" cross section is provided beneath cantilevered upper surface 12 and lower surface 13, for insertion of absorbent fabric or sponge barrier members 15 to collect and prevent the spread of topical antiseptic solutions beyond an area defined by opening 11 within barrier housing 10.

Moreover, prior to use, an adhesive layer 16 adjacent to lower body facing surface 13 attaches hollow pouch 10 to a surface of a person having surgery to be done. Opening 11 exposes the portion of the skin to be prepared with a topical antiseptic which is then applied. Excess topical antiseptic solution is then absorbed by spongy members 15 within hollow compartment 11a.

Figure 1C:
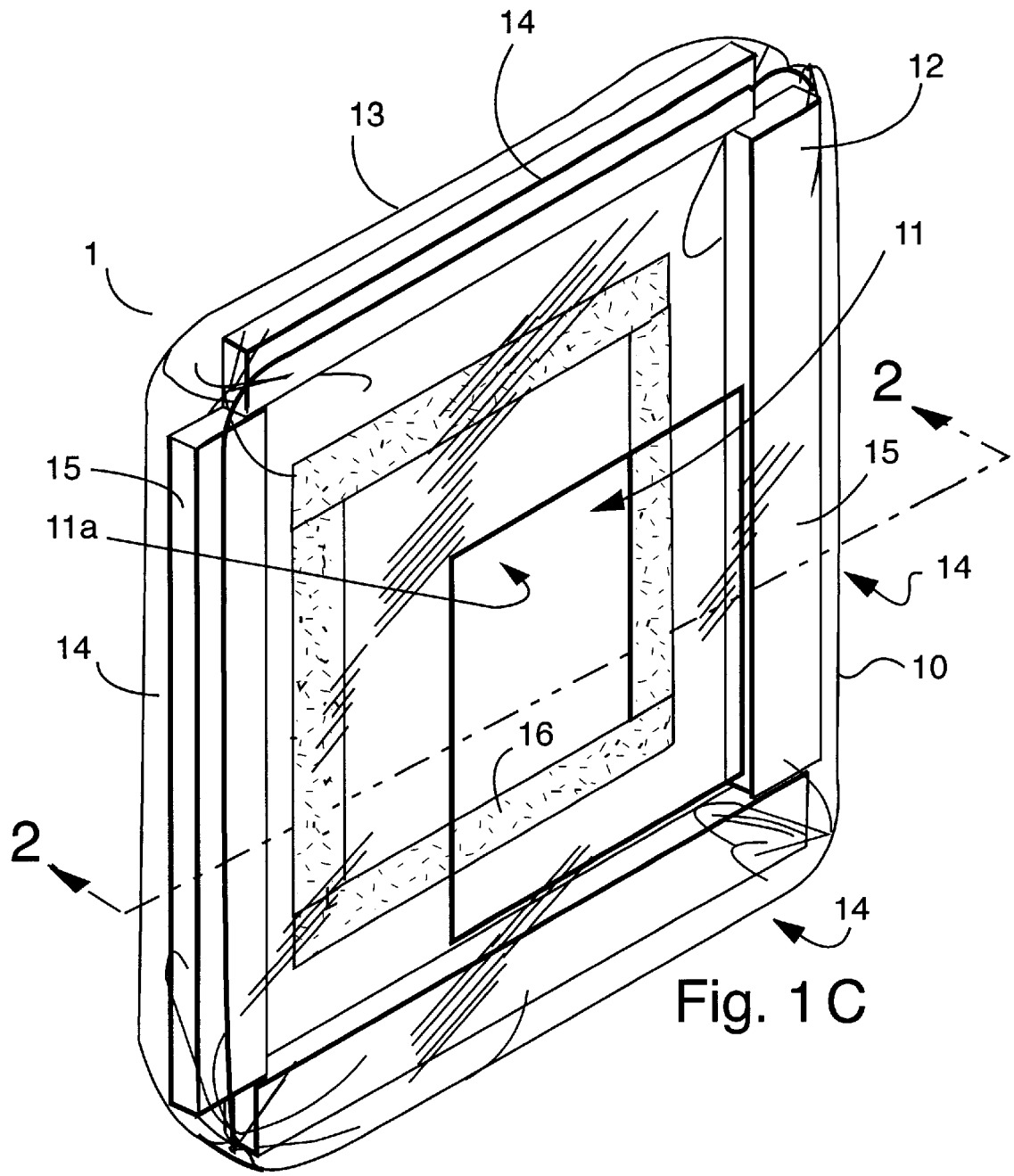
FIG. 1C is an isometric view of an alternate embodiment for a transparent surgical preparation protective barrier device of the present invention, shown in partial cutaway.
Figure 2C:
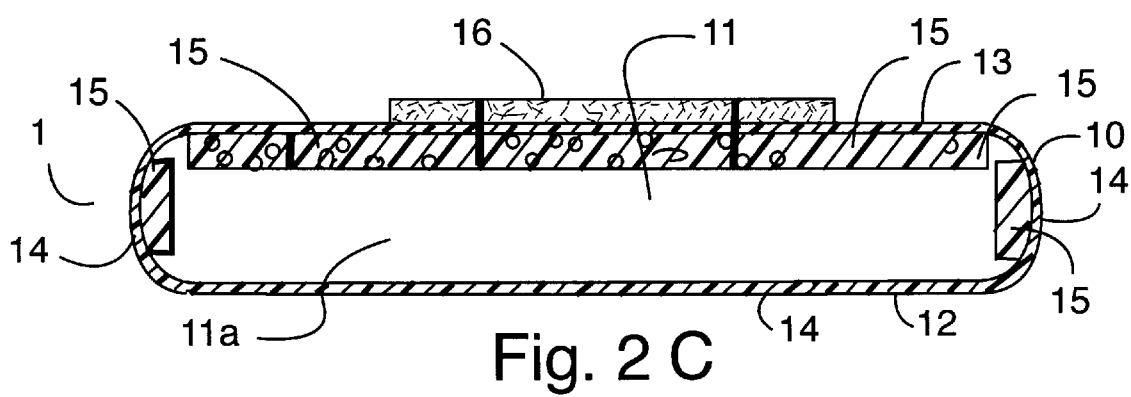
FIG. 2C is a cross sectional view thereof, taken at line "2—2" therein.

Barrier housings 10, 110 or 210 may be opaque as in FIGS. 1A, 2A, 1B and 2B, or for better viewing, may be transparent as in FIGS. 1C and 2C.

Figure 4:
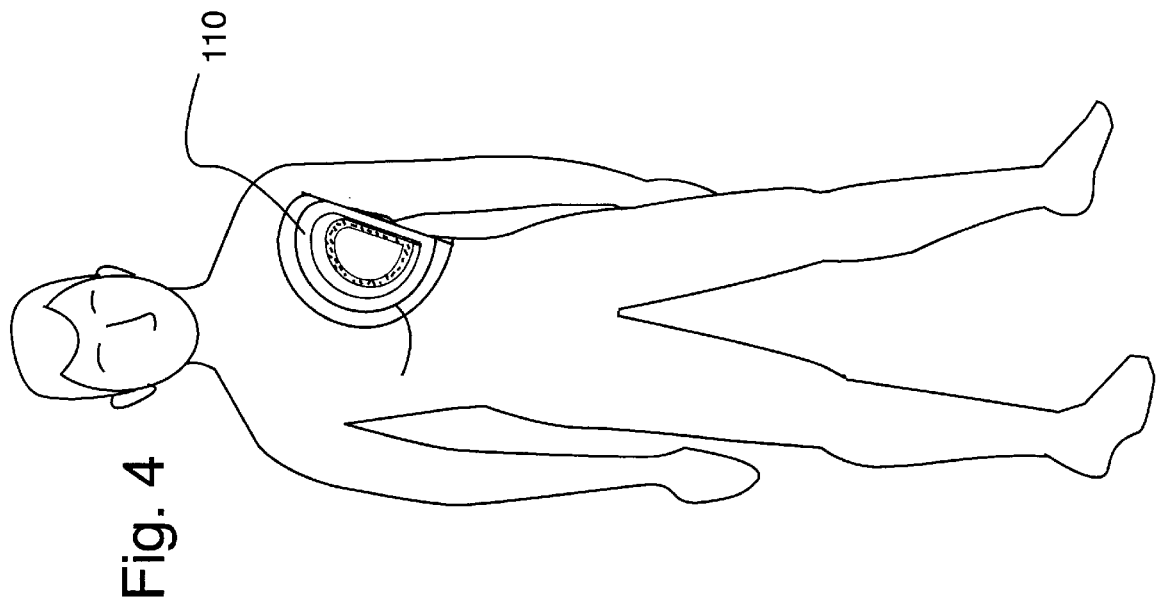
FIG. 4 is an isometric view of another embodiment for a surgical preparation protective barrier device, shown in use upon a chest of a patient, wherein the patient is shown for environmental purposes only.
Figure 3:
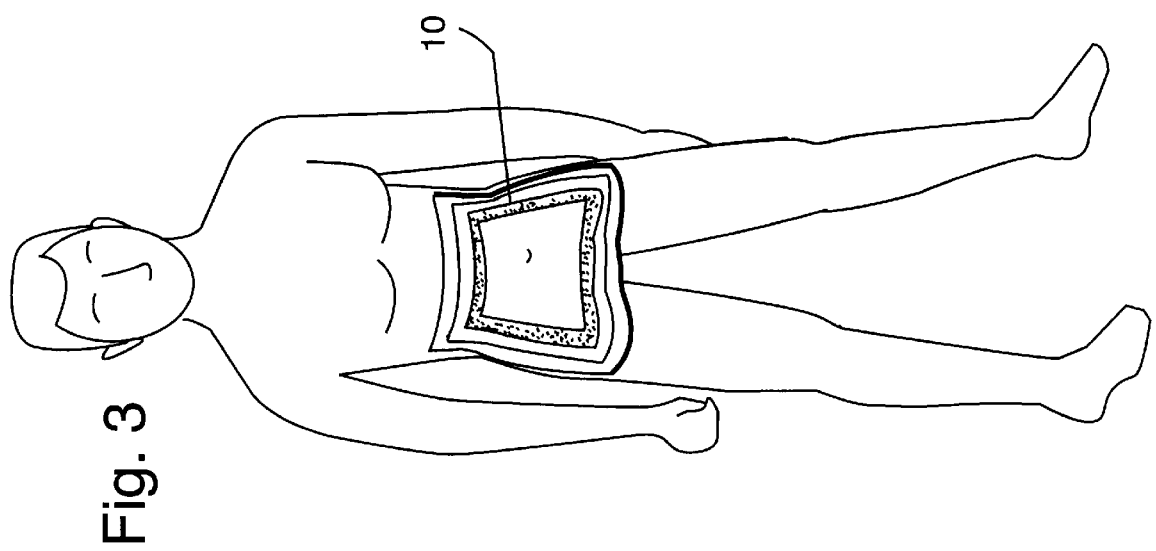
FIG. 3 is an isometric view of a surgical preparation protective barrier device of the present invention, as in FIG. 1A, shown in use upon an abdomen of a patient, wherein the patient is shown for environmental purposes only.

Barrier device 1 is designed to be appropriate for all types of procedures and will therefore by definition be of various shapes and sizes. For example, FIG. 3 shows square shaped barrier housing 10, flat anatomical areas such as, in abdominal surgery FIG. 4 shown circular barrier housing 110 for arcuate anatomical areas, such as chest or shoulder areas.

Figure 6:
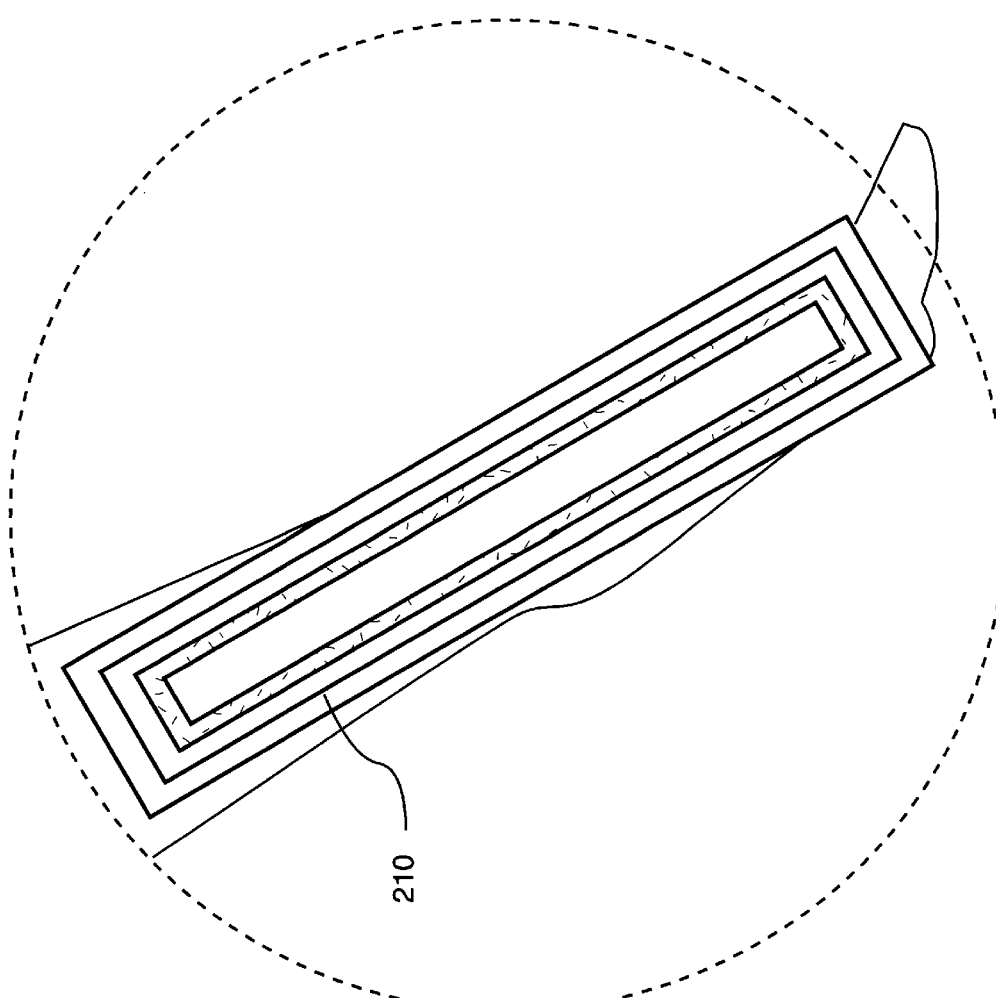
FIG. 6 is a closeup view thereof, shown in use upon a leg of a patient, wherein the patient's leg is shown for environmental purposes only.
Figure 5:
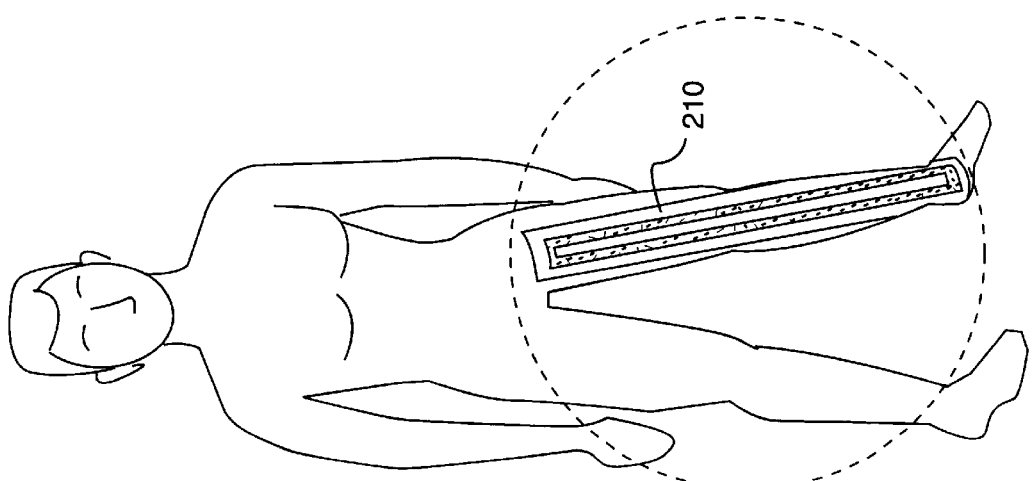
FIG. 5 is an isometric view of another further embodiment for a surgical preparation protective barrier device, shown in use upon a leg of a patient, wherein the patient's leg is shown for environmental purposes only.

FIGS. 5 and 6 show rectangular barrier housings 210 for longitudinally extending anatomical areas, such as limbs, in such surgeries as saphenous vein harvesting for cardiac bypass surgery. These configurations allow applications to the head and neck, back and thorax, abdomen and pelvis, and upper and lower extremities. The simple configuration and non sterile nature of barrier device 1 decreases patient infectious and irritant morbidity, thus preventing "BETADINE burns" that invariably occur when a topical antiseptic flows beyond a predefined surgical site and pools at a lower peripheral skin edge for an excessive period of time during surgery.

It is further noted that other modifications may be made to the present invention, without departing from the scope of the invention, as noted in the appended claims.

I claim:

1. A protective barrier device to prevent the spread of the surface flow of a topical antiseptic from beyond a predetermined surgical site comprising:

a hollow vouch having an opening extending therethrough, said opening defining the boundaries of the predetermined surgical site;

said hollow pouch further having an upper surface separated from a lower surface by at least one peripherally extended wall, wherein said opening extends between said upper surface and said lower surface;

said hollow pouch further having a hollow compartment under said upper surface and above said lower surface;

said hollow compartment having at least one fluid absorbent member therein for absorbing the flowing topical antiseptic therein;

said hollow pouch having a skin adhering adhesive on said lower, body facing surface, wherein said upper surface extends in a cantilevered manner away from said at least one peripherally extending wall toward said opening.

2. The protective barrier device as in claim 1 wherein said at least one outer wall is a circumferentially extending wall.

3. The protective barrier device as in claim 1 further comprising a removable cap layer covering said opening prior to use.

4. The protective barrier device as in claim 3 wherein said hollow pouch is circular.

5. The protective barrier device as in claim 2 wherein said at least one outer wall is plurality of walls defining a geometric shaped member.

6. The protective barrier device as in claim 5 wherein said geometrically shaped member is square.

7. The protective barrier devices as in claim 5 wherein said geometrically shaped member is rectangular.

8. The protective barrier device as in claim 2 wherein said at least one fluid absorbent member is an absorbent fabric.

9. The protective barrier as in claim 2 wherein said at least one fluid absorbent member is a sponge.

10. The protective barrier device as in claim 2 wherein said hollow compartment is substantially C-shaped in cross section.

11. The protective barrier device as in claim 2 wherein said adhesive is coated upon said body facing lower surface of said hollow pouch.

12. The protective barrier device as in claim 2 wherein said hollow pouch is made of vinyl.

13. The protective barrier device as in claim 2 wherein said hollow pouch is made of polypropylene.

14. A protective barrier device to prevent the spread of the surface flow of a topical antiseptic from beyond a predetermined surgical site comprising:

a hollow pouch having an opening extending therethrough, said opening defining the boundaries of the predetermined surgical site;

said hollow pouch further having an upper surface separated from a lower surface by at least one peripherally extended wall, wherein said opening extends between said upper surface and said lower surface;

said hollow pouch further having a hollow compartment under said upper surface and above said lower surface;

said hollow compartment having at least one fluid absorbent member therein for absorbing the flowing topical antiseptic therein; and, said hollow pouch having a skin adhering adhesive on said lower, body facing surface, wherein said hollow pouch is transparent.

15. The protective barrier device as in claim 2 wherein said hollow pouch is a hollow toroid, said hollow toroid having a larger outer diameter surface and a smaller inner diameter surface, said smaller inner diameter surface having an opening to said hollow compartment.

16. The protective barrier device as in claim 2 wherein said hollow pouch includes a plurality of joined hollow longitudinally extending C-shaped members, wherein further each open portion of each C-shaped member faces inward toward said opening of said hollow pouch.

17. The protective barrier device as in claim 2 wherein said hollow pouch is non-sterile.

18. The protective barrier device as in claim 14 further comprising a removable cap layer covering said opening prior to use.

19. The protective barrier device as in claim 14 wherein said at least one outer wall is a circumferentially extending wall.

20. The protective barrier device as in claim 19 wherein said hollow pouch is circular.

21. The protective barrier device as in claim 14 wherein said at least one outer wall is plurality of walls defining a geometric shaped member.

22. The protective barrier device as in claim 21 wherein said geometrically shaped member is square.

23. The protective barrier devices as in claim 21 wherein said geometrically shaped member is rectangular.

24. The protective barrier device as in claim 14 wherein said at least one fluid absorbent member is an absorbent fabric.

25. The protective barrier as in claim 14 wherein said at least one fluid absorbent member is a sponge.

26. The protective barrier device as in claim 14 wherein said hollow compartment is substantially C-shaped in cross section.

27. The protective barrier device as in claim 14 wherein said adhesive is coated upon said body facing lower surface of said hollow pouch.

28. The protective barrier device as in claim 14 wherein said hollow pouch is made of vinyl.

29. The protective barrier device as in claim 14 wherein said hollow pouch is made of polypropylene.

30. The protective barrier device as in claim 14 wherein said hollow pouch is a hollow toroid, said hollow toroid having a larger outer diameter surface and a smaller inner diameter surface, said smaller inner diameter surface having an opening to said hollow compartment.

31. The protective barrier device as in claim 14 wherein said hollow pouch includes a plurality of joined hollow longitudinally extending C-shaped members, wherein further each open portion of each C-shaped member faces inward toward said opening of said hollow pouch.

32. The protective barrier device as in claim 14 wherein said hollow pouch is non-sterile.

* * * * *